(12) United States Patent
Kerr et al.

(10) Patent No.: US 8,930,226 B1
(45) Date of Patent: *Jan. 6, 2015

(54) GATHERING, STORING, AND RETRIEVING SUMMARY ELECTRONIC HEALTHCARE RECORD INFORMATION FROM HEALTHCARE PROVIDERS

(71) Applicants: Gordon Stewart Kerr, Chicago, IL (US); Gregory Stewart Kerr, Chicago, IL (US)

(72) Inventors: Gordon Stewart Kerr, Chicago, IL (US); Gregory Stewart Kerr, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,346

(22) Filed: Apr. 30, 2013

Related U.S. Application Data

(63) Continuation-in-part of application No. 12/837,598, filed on Jul. 16, 2010, now Pat. No. 8,452,617, which is a continuation of application No. 12/642,907, filed on Dec. 21, 2009, now Pat. No. 8,285,565.

(51) Int. Cl.
*G06F 19/00* (2011.01)

(52) U.S. Cl.
CPC .................................. *G06F 19/322* (2013.01)
USPC .......................................................... 705/3

(58) Field of Classification Search
CPC ... G06F 19/322; G06F 19/3418; G06Q 50/24; G06Q 50/22
USPC .......................................................... 705/3
See application file for complete search history.

(56) References Cited

U.S. PATENT DOCUMENTS

| | | |
|---|---|---|
| 5,903,889 A | 5/1999 | de la Huerga et al. |
| 7,124,031 B1 | 10/2006 | Hoffman et al. |
| 7,379,885 B1 | 5/2008 | Zakim |
| 7,437,302 B2 | 10/2008 | Haskell et al. |
| 7,490,046 B1 | 2/2009 | Wyatt |
| 7,499,866 B2 | 3/2009 | Summers et al. |
| 7,543,039 B2 | 6/2009 | Himmelstein |

(Continued)

FOREIGN PATENT DOCUMENTS

| | | |
|---|---|---|
| WO | 0007131 | 2/2000 |
| WO | 0079454 | 12/2000 |

(Continued)

OTHER PUBLICATIONS

First office action on the merits (Non-Final Rejection) in U.S. Appl. No. 12/642,907, sent on Dec. 21, 2011.

(Continued)

*Primary Examiner* — Michelle L Le
(74) *Attorney, Agent, or Firm* — The Law Office of Patrick F. O'Reilly III, LLC

(57) ABSTRACT

The system and method of the invention describes a unique approach to gathering patient treatment information in summary form from a universe of health care providers, each using any form of patient information management; converting that information to pointers that can be searched by a healthcare provider before or during treatment to determine if further information needs to be acquired from the original provider; and a variety of methods to provide access to detailed healthcare treatment and diagnosis information from the original provider through an access and display method provided by the Health Care Provider housing the records if available. The system and method envisages one or more providers of repository services, each offering various ways for healthcare providers to update and maintain summary information, and each providing for continual exchange of information among them to ensure complete access to all available information.

20 Claims, 4 Drawing Sheets

(56) References Cited

U.S. PATENT DOCUMENTS

| | | |
|---|---|---|
| 8,285,565 B2 | 10/2012 | Kerr et al. |
| 8,311,855 B2 | 11/2012 | Kerr et al. |
| 8,452,617 B2 | 5/2013 | Kerr et al. |
| 2001/0016822 A1 | 8/2001 | Bessette |
| 2003/0046114 A1 | 3/2003 | Davies et al. |
| 2003/0163483 A1 | 8/2003 | Zingher et al. |
| 2003/0191669 A1 | 10/2003 | Fitzgerald et al. |
| 2004/0128163 A1 | 7/2004 | Goodman et al. |
| 2004/0128165 A1 | 7/2004 | Block et al. |
| 2005/0021376 A1 | 1/2005 | Zaleski et al. |
| 2005/0076158 A1 | 4/2005 | Kwon |
| 2005/0086071 A1 | 4/2005 | Fox, Jr. et al. |
| 2005/0209890 A1 | 9/2005 | Kong |
| 2006/0026034 A1 | 2/2006 | Yankelevitz et al. |
| 2006/0026043 A1 | 2/2006 | Schneider et al. |
| 2006/0116908 A1 | 6/2006 | Dew et al. |
| 2006/0155584 A1 | 7/2006 | Aggarwal |
| 2006/0229918 A1 | 10/2006 | Fotsch et al. |
| 2008/0052113 A1 | 2/2008 | Cauley et al. |
| 2008/0201174 A1 | 8/2008 | Ramasubramanian et al. |
| 2008/0228746 A1 | 9/2008 | Markus et al. |
| 2008/0270191 A1 | 10/2008 | Beeckel et al. |
| 2008/0287746 A1 | 11/2008 | Reisman |
| 2008/0306926 A1 | 12/2008 | Friedlander et al. |
| 2009/0150185 A1 | 6/2009 | Lassetter et al. |
| 2010/0088346 A1 | 4/2010 | Urness et al. |

FOREIGN PATENT DOCUMENTS

| | | |
|---|---|---|
| WO | 0198866 | 12/2001 |
| WO | 02052483 | 7/2002 |
| WO | 2007106183 | 9/2007 |
| WO | 2008147566 | 12/2008 |

OTHER PUBLICATIONS

Notice of Allowance in U.S. Appl. No. 12/642,907, mailed on Jun. 12, 2012.

Notice of Allowance in U.S. Appl. No. 12/957,895, mailed on Aug. 3, 2012.

First Supplemental Notice of Allowance in U.S. Appl. No. 12/642,907, mailed on Jul. 25, 2012.

Second Supplemental Notice of Allowance in U.S. Appl. No. 12/642,907, mailed on Aug. 27, 2012.

First office action on the merits (Non-Final Rejection) in U.S. Appl. No. 12/837,598, mailed on May 29, 2012.

Notice of Allowance in U.S. Appl. No. 12/837,598, mailed on Jan. 31, 2013.

Chesapeake Regional Information System for Our Patients (CRISP): A Plan for Citizen-Centric Statewide Health Information Exchange in Maryland (Presented to the Maryland Health Care Commission and Health Services Cost Review Commission), Web page <http://mhcc.dhmh.maryland.gov/hit/hie/Documents/CRISP_FinalReport.pdf>, 96 pages, dated Feb. 2009, retrieved from Maryland Department of Health and Mental Hygiene Website <http://mhcc. dhmh. maryland.gov/> on Aug. 20, 2014.

GATHERING, STORING, AND RETRIEVING SUMMARY ELECTRONIC HEALTHCARE RECORD INFORMATION FROM HEALTHCARE PROVIDERS

CROSS-REFERENCE TO RELATED APPLICATIONS

This is a continuation-in-part of U.S. patent application Ser. No. 12/837,598, filed Jul. 16, 2010, which is a continuation of application Ser. No. 12/642,907, filed Dec. 21, 2009; the disclosure of each of which is hereby incorporated by reference as if set forth in their entirety herein.

A portion of the disclosure of this patent document contains material which is subject to copyright protection. The copyright owner has no objection to facsimile reproduction by anyone of the patent documentation or the patent disclosure, as it appears in the Patent & Trademark Office patent file or records, but otherwise reserves all copyright rights whatsoever.

FIELD OF THE INVENTION

The field of the invention relates to medical record search and retrieval, the management of patient record information, and diagnostic services for healthcare providers.

BACKGROUND OF THE INVENTION

Healthcare providers manage patient treatment information in a variety of forms, ranging from completely automated electronic healthcare record management systems to paper files. Discovery of possibly significant information about a patient is ineffective and likely to be incomplete since most patients utilize a variety of providers which in turn utilize a variety of incompatible record management systems. Searching for medically relevant records for a particular patient is hampered by the number of previous healthcare providers that have treated a patient, and likely to be dangerously incomplete. A recent US government initiative to compel all healthcare providers to implement electronic healthcare record management systems by 2014 does not address and will not solve the problem of identifying all previous treatment and diagnosis information.

There are numerous reasons why a simple search of the web using Google, Bing, Yahoo or any other search engine would not provide equivalent results to the invention. First, search engines focus on public information openly displayed on searchable pages. A search for a patient identifier such as its social security number ("SSN") might return thousands of records containing that number in completely unrelated web pages, even assuming that the medical record information were exposed and indexed by search engines. But health care records must be protected by adequate security, behind at least password protected barriers. In order to search electronic health care record systems each search engine would have to have gained access to those systems with appropriate security measures. Consequently, simple searchers would have to be particularized to specific web sites corresponding to health care providers, which is a feature of the invention but not available in search engines since they assume they will search all web pages not restricted by the convention "nosearch" on the page URL.

Second, even if search engines had particularized, security controlled access to a defined set of health care provider systems, the patient identifier would not necessarily be the first information in a record, or in a standard location. The search engines would have to do a deep search of every record in every system looking for all occurrences of the patient identifier or SSN. This would depend on patient identifier numbers being readily found and identified, and could also return records for dependents, parents, or other relatives included, meaning that the results of the search could be incomplete or overloaded with possibly extraneous records. Information on date of service and diagnostic code or prescription information would also have to be deduced from the contents of each record.

Third, results returned would be incomplete since the majority of health care providers have not converted to electronic health care record systems, and have no medical record information to offer up to a search engine. A federal requirement is that all health care providers must use such systems by 2014, but there is no requirement for providers to convert all older records. Consequently, even if a particularized search was available, and patient identifiers could identify records of interest, this would not reach all health care providers until 2014 at the earliest, and would not necessarily provide records of previous health care records.

Finally, even if there were a particularized and secure search of health care providers available, and even if the basic information of patient ID, date of service and diagnostic code could be found by searching records, and even if all health care providers had converted to electronic record management systems, and even if those records could be returned in a consistent form, the variety of electronic health care record formats would make the results difficult to scan for particular information, difficult to search in date order, and difficult to easily determine which records may be of interest based on the diagnostic or treatment code, since records and record fields will vary from system to system.

SUMMARY OF EMBODIMENTS OF THE INVENTION

The system and method of the invention contemplates one or more repositories of medical record information, or Medical Records Registration and Management systems, to compile summary patient treatment and diagnosis information that can serve as pointers or references from any and all Health Care Providers, containing at a minimum unique patient identifiers (Social Security Number or alien identifier), date of service, Health Care Provider identifier, diagnostic code or diagnosis, and optionally billing codes associated with the provision of health services.

In addition, each repository would contain or have access to a database of Health Care Providers, current and past diagnostic codes and billing codes, and information or technical indicators determining whether the Health Care Provider electronic system of Electronic Healthcare Records (if any) could be accessed directly by another Health Care Provider.

The method of the invention would allow for a rapid search of all repositories, including Health Care Providers that act as their own repository of information, to find all Electronic Healthcare Records pointers or references and summaries, arranged by date. A Health Care Provider providing service to a patient could determine which records might be needed to properly treat the patient by date of service and diagnosis, and possibly billing code. If the Health Care Provider with the patient Electronic Healthcare Records has a direct or browser based access to those records, the Health Care Provider could access them directly.

The system and method is completely general in that it allows for a multitude of Medical Records Registration and Managements, does not require a massive and expensive conversion to a common system to improve health care management (reference to failed UK Electronic Healthcare Records system), encourages new and increasing effective ways to store and retrieve Electronic Healthcare Records without reducing the effectiveness of the invention, allows for security and HIPAA compliance processes now in place or that may be defined to be incorporated, and places patient health care uppermost.

The system and method is unique and unprecedented in that it reverses the thinking that all Electronic Healthcare Records would need to be translated into a common standard format, and possibly centralized to achieve uniform and complete access to Electronic Healthcare Records. That approach would require years if not decades to implement in any meaningful way, i.e. comprising more than 80% of Electronic Healthcare Records, and would depend on the time consuming and usually contentious process of setting industry standards for Electronic Healthcare Records.

Instead, the system and method of the invention simply provides a pointer to Electronic Healthcare Records and where the detailed information in the Electronic Healthcare Records are stored, along with basic information to allow Health Care Providers to determine whether the Electronic Healthcare Records may be relevant, and whether they may be accessed in some electronic form, or must be accessed through less efficient means such as fax or even phone conversations.

Additional features and characteristics of the invention are that it is: (a) Based on the point of view of the recipient of medical treatment, the patient, and the immediate Health Care Provider, to maximize the value of Electronic Healthcare Records in treating the patient; (b) Provides for organization and identification of medical data, records and information (Electronic Healthcare Records) without specific action by the patient; and (c) Allows for registration by Social Security Number or Alien registration number as a universal identifier.

Specific Attributes of the Invention include: (a) pointer records or reference data may be transferred in their entirety by the original Health Care Providers to one of many providers of Electronic Healthcare Records based on Social Security Number or unique identifier; (b) Health Care Providers may choose to record that patient Electronic Healthcare Records are stored on their system and are available for access, transfer and/or review with proper access rights established; (c) Existence of Electronic Healthcare Records can be established at one, some or all of the providers of Medical Records Registration and Management; (d) Medical Records Registration and Management providers can accept records in multiple formats according to their capabilities, or only record the provider identification and the access path for the records; (e) Medical Records Registration and Management providers may allow for PDF documents, scanned images, recordings, faxes, lab results in many electronic forms, and other current or future available formats; (f) Does not require a single centralized provider of medical information, and in fact would encourage competition to act as a repository; (g) Does not require translation or conversion of Electronic Healthcare Records into some standard format, thus allowing all existing systems to continue in use without expensive upgrades; (h) Allows for redundancy of storage for Electronic Healthcare Records across providers of Medical Records Registration and Management; and (i) Encourages Electronic Healthcare Records providers and software providers for the medical market to establish common access processes or APIs that would allow medical practitioners to access patient information without regard to the system containing the information.

The method of the invention provides a simple and easily implemented way for any and all health care providers to indicate the existence of records for a patient, without necessarily having to convert old records from paper, and without requiring all health care providers to have electronic record keeping systems in order to indicate the availability of patient information. The invention provides a consistent, powerful and complete approach to gathering and presenting summary records, or pointers, to possibly relevant information contained in a multiplicity of forms by all health care providers regardless of which if any electronic record keeping system they have.

Numerous advantages and features of the invention will become readily apparent from the following detailed description of the invention and the embodiments thereof, and from the accompanying drawings.

BRIEF DESCRIPTION OF THE DRAWINGS

A fuller understanding of the foregoing may be had by reference to the accompanying drawings, wherein.

DETAILED DESCRIPTION OF EMBODIMENTS OF THE INVENTION

Figure 1:
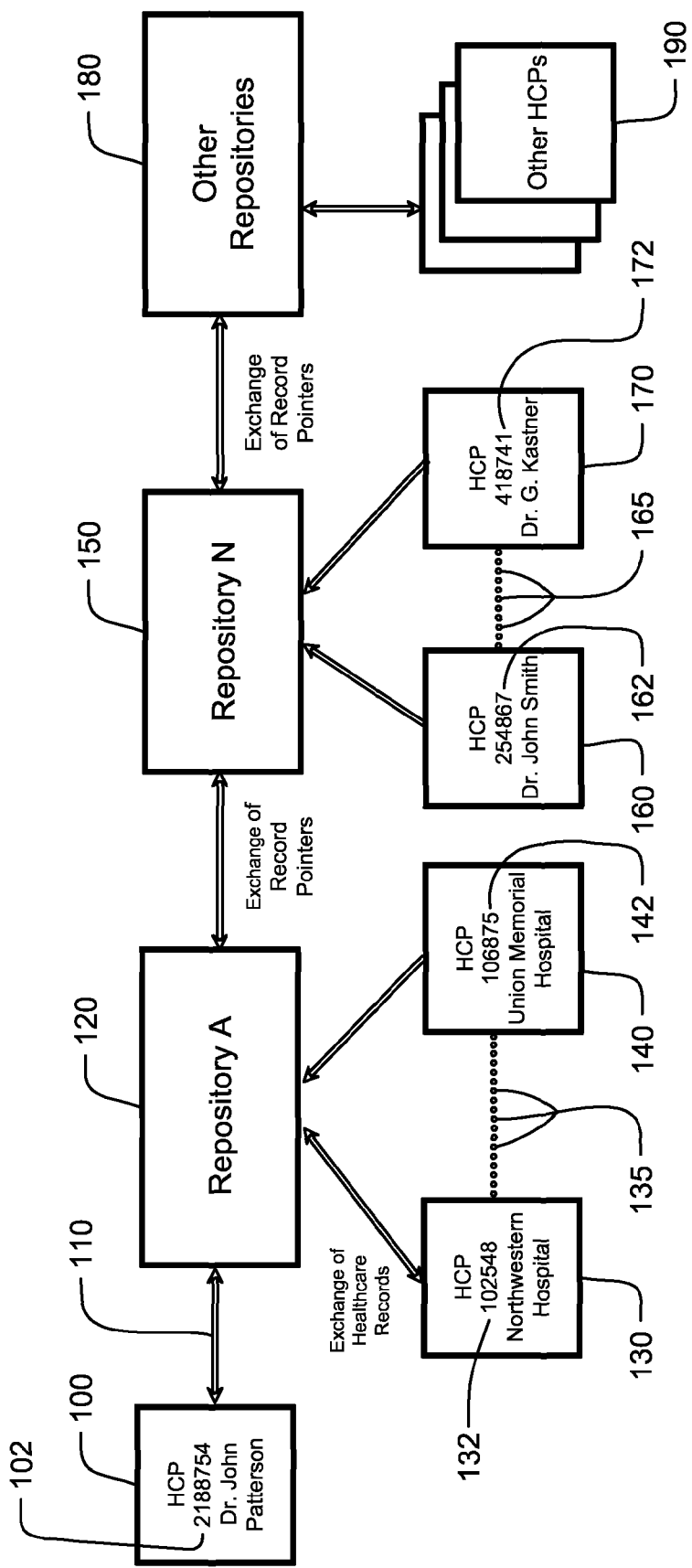
FIG. 1 is a general schematic overview of the invention illustrating the connection between repository databases and healthcare providers.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the claims by the embodiments illustrated.

The following terms are used herein with their accompanying definitions:

Repository (Database)—one or more structured sets of persistent data, usually associated with software to update and query the data. A simple repository might be a single file containing many records, each of which is structured using the same set of fields. A repository can comprise a map wherein various identifiers are organized according to various factors, such as identity, physical location, location on a network, function, etc.

Active Link—a link on a page that allows a user to access a particular function by activating the active link through an action such as a keyboard stroke or mouse click. Activation of an active link can occur through a "single action", which as used herein refers to any single act that can activate a function, such as a mouse click, a mouseover, a keyboard stroke, a pen stroke, a finger stroke or signal, a voice signal, staring at a predetermined screen location for a predetermined time, and/or any equivalents thereof.

Identifier—a group of symbols that are unique to a particular entity, activity, and/or document. An identifier can be, for example, a medical record number. An identifier can be human and/or machine readable, such as for example, a number, an alphanumeric string, a bar code, an RFID, etc.

Patient or Healthcare Identifier or ID—an identifier for a particular patient or healthcare organization. A patient identifier might be a social security number, taxpayer ID number, national ID number, Medicare number, Medicaid number, medical insurance ID number, medical record number, etc. A Healthcare Provider Identifier or ID might be a tax or FEIN number, etc.

Repository identifier—an identifier for a particular repository to which one or more patient monitoring devices are linked.

Information device—a device capable of processing information, such as any general purpose and/or special purpose computer, such as a personal computer, workstation, server, minicomputer, mainframe, supercomputer, computer terminal, laptop, phone, and/or any equivalents thereof, etc.

Interface—a boundary across which two independent systems meet and act on or communicate with each other. To connect with or interact with by means of an interface.

Machine-readable media—a memory readable by an information device.

Memory—a device capable of storing analog or digital information, for example, a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory can be coupled to a processor and can store instructions adapted to be executed by processor according to an embodiment disclosed herein.

Network—a wired and/or wireless communication network.

Network interface—a telephone, a cellular phone, a cellular modem, a telephone data modem, a fax modem, a wireless transceiver, an Ethernet card, a cable modem, a digital subscriber line interface, a bridge, a hub, a router, or other similar device.

Patient—a human or other type of animal under supervision for health care purposes.

Patient or medical information—information relevant to the medical care and/or treatment of a patient, including real-time vital, biological, and/or physiological data, near real-time and/or prior history data relating to vital, biological, and/or physiological data, blood pressure parameters, ventilation parameters, vital sign parameters, blood oxygen concentration representative parameters, infusion pump parameters associated with fluid delivery, drip medication related parameters, blood gas parameters, insurance information, health care personnel information, health care organization information, billing information, family information, financial information, therapy information, drug information, and/or any equivalents thereof, etc.

Processor—a device and/or set of machine-readable instructions for performing a task. A processor comprises any one or combination of hardware, firmware, and/or software. A processor acts upon information by manipulating, analyzing, modifying, converting, transmitting the information for use by an executable procedure and/or an information device, and/or routing the information to an output device. A processor may use the capabilities of a controller.

Server—an information device that provides some service for other information devices connected to it via a network. A common example is a file server, which has a local disk and services requests from remote clients to read and write files on that disk. A server can also provide access to resources, such as programs, shared devices, etc.

Uniform resource locator (URL)—a standard way of specifying the location of an object, such as a web page, on the Internet, a network, and/or a server connected thereto. A URL can comprise a data field that comprises one or more identifiers.

User interface—a device and/or program for rendering information to a user and/or requesting information from the user. A user interface can include textual, graphical, audio, video, animation, and/or haptic elements.

User—an individual capable of utilizing a system for accessing patient information.

This section describes in general form the computer programs needed to implement a comprehensive national data base of health care record information. Any competent practitioner in field of information technology could construct a system using this description.

The principal idea of the system of the invention conceives a multitude of healthcare record repositories that would contain constantly updated pointers or vectors that signify the existence of information on a patient, and sufficient information for a health care professional to access the information online (if the originating healthcare provider offers online access) or to provide standardized request processes for asking for the records.

The descriptions below outline how the necessary computer programs would need to be constructed by a normally competent programmer or systems development company. Thus, as used herein, it is to be understood that, when a computer, computing device or data processing system is said to be configured and arranged to perform one or more steps or functions, this is equivalent to reciting that the computer or data processing system is specifically programmed or specially programmed to carry out the one or more steps or functions. Access to information within the repositories would be controlled and limited according to accepted computer security methods and consistent with any applicable government regulations and controls. These security controls are assumed to be readily available and are not described.

Exemplary Computer System Components

In one or more embodiments, an exemplary implementation for a Healthcare Provider is a basic personal computer or PC with an internet connection that enables a health care provider to access information in one of the exemplary healthcare record repository systems. In these embodiments, information requests to the repository system are formulated in a browser on the PC and sent to the repository system as an HTTP transaction.

Another exemplary implementation could include a number of personal computers or other terminal display devices connected to a medical records system serving the health care provider's location, either as a locally installed and operating server with one or more microprocessors, disk storage, wireless and internet connectivity mechanisms enabling a health care provider to use a PC, iPad, tablet or other device that could connect wirelessly to the local server. The local server would then establish an internet connection to one of the health care repositories with the request for information for a particular patient.

In both of these exemplary implementations, the information response from the repository server would be as described in detail hereinafter, namely one of: a URL link to view one or more health care records, a direct link to a health care provider's electronic record management system with appropriate security access controls, or information on how to request the appropriate information including a request form, a telephone or fax number.

One possible system implementation for an exemplary health care record repository system could include one or more microprocessor servers, one or more disk drives containing health care records, one or more internet connections to receive inbound requests from health care providers and, as and when available, to obtain electronic images from one health care provider system to display to a requesting provider.

As described in further detail hereinafter, an exemplary repository system could also provide health care records management storage as a service to one or more health care providers. In this case, the records would be provided directly from the disk storage on the repository system.

In addition, there are of course many other possible implementations available to health care providers and repository managers, including cloud based services such as Amazon® Web Services or Google® App Engine, and "platform as a service" offerings from Rackspace®, IBM® and many others.

Basic Information Contained in Repositories

For every patient and every treatment event, diagnostic test or medical procedure, a summary record is created by the original Healthcare Provider (HCP) with the following basic information: (a) Healthcare Provider Identifier, (b) Patient ID, (c) Date of Service, and (d) Diagnosis and/or Billing code. The Healthcare Provider Identifier is a unique identification number that helps to identify the Healthcare Provider from each other Healthcare Provider. The Patient ID, may be the patient's SSN or another alien identification number, identifies the patient from other patients, and from related family members. The Diagnosis and/or Billing Code are codes widely used in the medical field help to identify the type of treatment, procedure, or tests, conducted by the Healthcare provider.

These records are referred to as pointers or vectors because they serve to locate more detailed information about the patient, the healthcare provider, and health care information available including test results, recordings, radiology scans, etc. These records are further stored on memory in a Repository or Database.

Every Healthcare Provider (HCP) can select from a multitude of Repository service providers (REP) that maintain one or more Repositories to accept and maintain the HCP record pointers. The selection would be based on any commercial basis including cost and ease of use for the HCP staff. The existence of multiple suppliers acting as Repositories will encourage competition and innovation, as opposed to a single, central repository whether privately operated or governmental such as SSA.

Automated, semi-automated or manual data entry programs gather the data from each HCP and transmit the data to a dedicated REP, which in turn shares that information with all other REPs using a process similar to how search databases operate. REPs maintain a database listing all other REPs along with access information to allow secure exchange of healthcare record pointers among REPs. REPs scan all other REPS on a periodic basis to compile a database of all healthcare record pointers. Each REP has comprehensive, up to date information available to the HCPs to which they provide service. REPs also maintain databases of billing codes (current and previous), and indicators about how records in each HCP can be viewed or accessed by another HCP, i.e. access method to be employed to see detailed information, electronic records, even x-rays and EKGs if available from the original provider. REPs may provide additional services to HCPs including maintaining original healthcare records and test results, providing interface programs to allow for automated collection and transmission of healthcare records, and access programs that allow HCP staff to directly access healthcare records at other HCPs using special purpose programs that do not require detailed information about other HCP systems. These programs may be direct view or direct access or may be browser based.

As illustrated in FIG. 1, a general description of the system and method for multiple repositories and health care providers is illustrated. For example, every Healthcare Provider Selects a Repository Provider to act as an Intermediary to any other Healthcare Provider searching for patient records. In this example diagram, Dr. John Patterson (box 100) has selected (line 110) Repository A (box 120) to be its provider of record pointers and its access point to search for and view health care records for its patients. Repository A (box 120) also provides services to Northwestern Hospital (box 130) and Union Memorial Hospital (box 140), among others, as indicated by the ellipsis (dots 135). Repository N (box 150) provides services to Drs. Smith (box 160) and Kastner (box 170) among others (dots 165). Other Respositories (box 180) would be linked to other HCPs (box 190). Each health care provider (100, 130, 135 140, 160, 165, and 170) would be assigned a unique HCP identifier (102, 132, 142, 162, 172, respectively) and exchanges information with their selected repository (120, 150) including record pointers and in some cases copies of medical records for storage on the repository.

Figure 4:
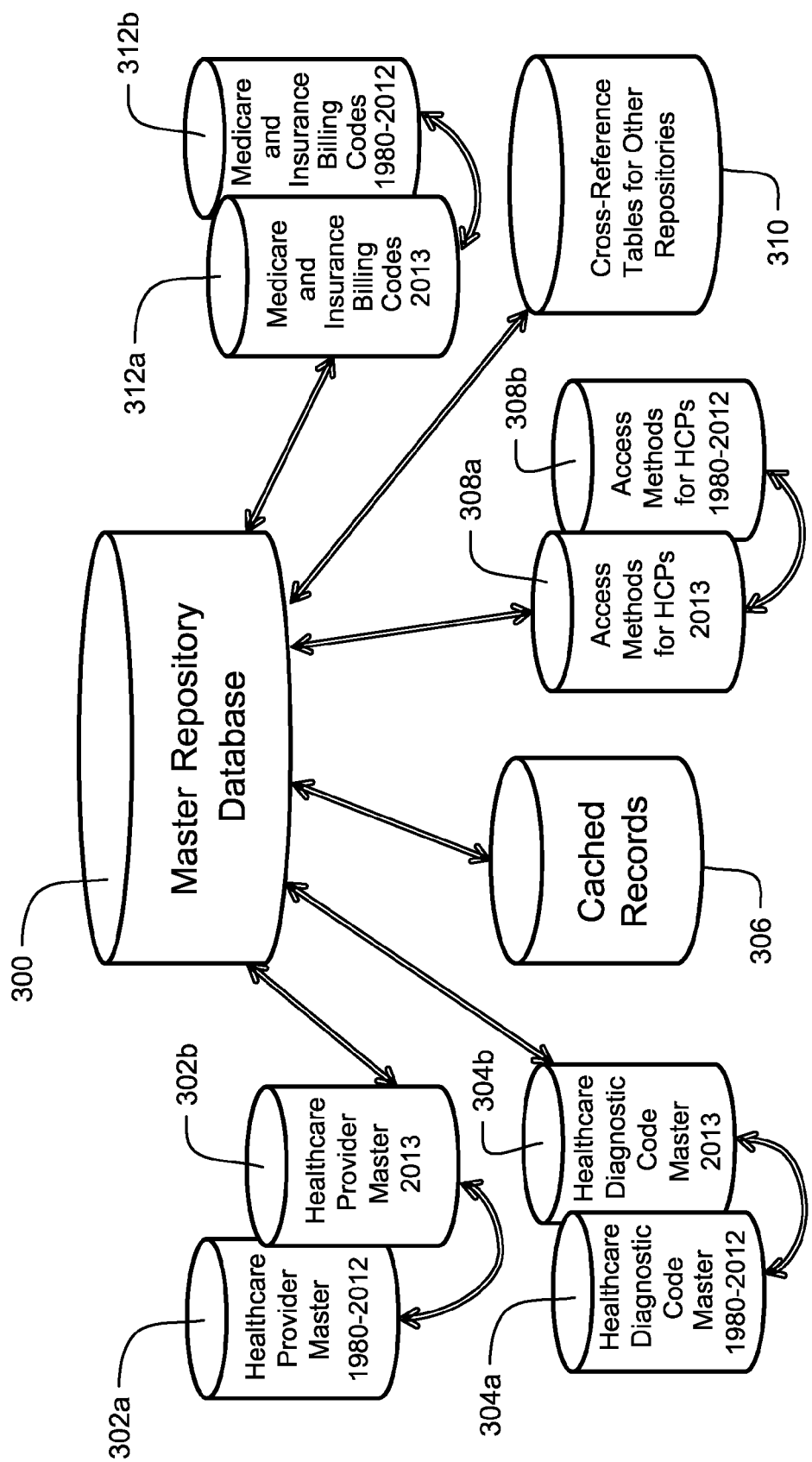
FIG. 4 is a schematic diagram illustrating an exemplary content of a master repository database.

In FIG. 4, exemplary content for a master repository database 300 is illustrated in schematic form. As shown in this figure, an exemplary master repository database 300 generally comprises a healthcare provider master database 302*a*, 302*b*; healthcare diagnostic code tables 304*a*, 304*b*; cached records 306; access method tables for each HCP 308*a*, 308*b*; cross-reference tables for other repositories 310; and lists or tables of Medicare and insurance billing codes 312*a*, 312*b*. While not explicitly illustrated in FIG. 4, the master repository database 300 may also contain stored records from some HCPs (if provided as a service by the Repository) and a cross-reference table for patient identifier numbers, which would preferably include patient names, name changes, and standard patient identifiers. Referring again to FIG. 4, it can be seen that the healthcare provider master database is segmented or partitioned into a component for previous years 302*a* (e.g., containing records for the years 1980 through 2012) and a current year component 302*b* (e.g., containing records for just the current year, namely 2013). Because doctors frequently move, the healthcare provider master database preferably contains historical data. The healthcare diagnostic code tables are similarly segmented or partitioned into a component for previous years 304*a* (e.g., containing records for the years 1980 through 2012) and a current year component 304*b* (e.g., containing records for just the current year, namely 2013). The healthcare diagnostic code tables are accessed based on the date of service.

With continued reference to FIG. 4, that the exemplary master repository database 300 also includes cached records 306 for those records that were most recently accessed. Similar to the healthcare provider master database 302*a*, 302*b* and the healthcare diagnostic code tables 304*a*, 304*b*, the access method tables for each HCP are segmented or partitioned into a current year component 308*a* (e.g., containing data for just the current year, namely 2013) and a component for previous years 308*b* (e.g., containing data for the years 1980 through 2012). The access method tables for each HCP are based on record type and date of service (some records may be in paper form before a certain date). As shown in FIG. 4, the master repository database 300 also preferably includes cross-reference tables for other repositories 310 for record exchange, including subset tables if some repositories keep records on a limited set of healthcare providers (i.e., an HCP can act as a repository manager if it is very large, such as an insurance provider or a regional hospital chain with a centralized record management system). As additionally shown in FIG. 4, the master repository database 300 includes lists or tables of Medicare and insurance billing codes that are segmented or partitioned into a current year component 312a (e.g., containing billing codes for just the current year, namely 2013) and a component for previous years 312b (e.g., containing billing codes for the years 1980 through 2012).

Major Processes

These are four major processes or computer programs involved in implementing the method of the invention. Each process could have many possible specific implementations, much as there are 10 or more commercially available web browsers, each implemented in a different technical form but each providing the same basic service with similar features and advantages. The four processes are: (a) Update Healthcare Provider Record Pointers in Repository HCP->REP; (b) Exchange Repository records with all other Repositories REP<—>REPS; (c) Search for Patient Records in the Repository HCP<—>REP; and (d) Obtain detailed information about particular records HCP<—>REP<—>HCP.

Update Healthcare Provider Record Pointers in Repository HCP->REP

Four program types would be available depending on the healthcare records management technology employed by a HCP. (1) Direct interface from HCP to REP; (2) Automated extract of HCP record pointers and upload to REP; (3) Manual data entry of HCP record pointers and upload to REP; and/or (4) Online data entry of HCP records into REP database.

In a Direct Interface from HCP to REP, the following steps would be taken: (a) Schedule daily or more frequent review of all of HCP records identifying all records that have been created or changed since the last review; (b) Build upload file with all new or changed records in standard format (Note: upload file could be a complete refresh of information to REP, even if technically inefficient, to ensure complete information exists on REP); (c) Prepare list of records that need diagnostic code or additional information; (d) If any records are incomplete, display list to HCP administrator, schedule additional review of all records; and (e) Send upload file to REP. This can be done over a direct or dedicated network connection between the HCP and REP repository.

In an Automated extract of HCP record pointers and upload to REP, the following steps would be taken: (a) Receive request from REP for update information or complete refresh of all HCP information. (Note: this process could also be scheduled for daily or more frequent review of all of HCP records identifying all records that have been created or changed since the last review); (b) Run export data preparation program, customized for each type of HCP system, to review all record information to ensure it is complete (Note: export file could be complete refresh of all information to REP as noted above); (c) Prepare list of records that need diagnostic code or additional information; (d) If any records are incomplete: (i) Display/print list to administrator; (ii) Wait for signal that records have been updated; (iii) Return to Step b; and Send export file to REP. This can be done over a network connection between the HCP and REP repository. In some instances the HCP would log onto a server and initiate a connection link between the HCP and REP and then initiate data transfer.

In a Manual data entry of HCP record pointers and upload to REP, the following steps are followed: (a) REP schedules daily or more frequent email to HCP; (b) HCP receives email and starts local program to enter information; (c) HCP enters record information for new or changed records; (d) HCP uploads information to REP; (e) REP checks each record for completeness or duplicates; (f) REP returns error listing to HCP; and (g) HCP corrects errors and uploads information to REP.

Lastly, an Online data entry of HCP records into REP database, would include the following steps: (a) REP schedules daily or more frequent email to HCP; (b) HCP receives email and clicks on link to enter data directly in REP system; (c) HCP enters record information; (d) REP checks each record for completeness or duplicates; (e) If incomplete or duplicate, REP shows error message to HCP, HCP corrects record; and (f) REP stores information.

In one or more embodiments, record pointers in the Repository include information sufficient to inform the treating health care provider or physician of the patient health care provider, patient identifier, date of service, type of service (billing code, diagnostic code, information type or treatment code) and a comment field. On receipt of an update record from a health care provider, the repository software would provide a number of data processing services, including but not limited to: (1) validating the health care provider identification, and expanding that information using stored repository databases to include physician name(s), address, telephone numbers etc.; (2) expanding the diagnostic and/or billing codes using stored repository databases to convert the coded information into a full description, e.g. diagnostic code 813.47 could expand into "813.47 Torus fracture of radius and ulna" (in 2012, the diagnostics were extended to include nearly 50,000 different diagnostic codes, making the addition of explanatory comments from the stored repository database important to the treating physician reviewing patient information in the repository); (3) expanding the billing codes using stored repository databases in a similar fashion, based on national databases of billing codes, to facilitate review by the treating physician; and (4) validating the access method associated with each repository record to ensure that the information can be accessed directly from the health care provider records management system, or that the URL in fact accesses the record, image or facsimile indicated. Once validated by the repository, these records could be maintained in the repository database, instead of requiring remote access to the information at the health care provider's system. For indirect methods of accessing the patient information, such as providing a telephone number or fax number, or filling in a request form, the repository could utilize various methods to ensure that telephone and fax numbers were accurate and up to date, and that the request form information could be completed based on information available to the repository.

Exchange Repository records with all other Repositories REP<—>REPS

Every Repository maintains a database of all healthcare records by regularly exchanging information with all other repositories, using a data base of repositories to scan for information. This process is similar to how search engines use bots to scan all websites for new web pages or information. The principal difference is that the information to be searched is behind a security screen and not available for general search or access without the appropriate security controls. The information is also in standard form, making the search and assembly of information straightforward.

Employing a typical search process against all HCPs would only gather information from those with automated systems. This process provides a means to gather information from all HCPs regardless of how or whether they employ automated records management systems.

Nevertheless, search bots are one of many possible methods to gather and exchange healthcare records from other repositories. Rather than describe the process used by search bots, it suffices to say that each repository would employ search bots to scan every repository listed in the data base of repositories and retrieve all new or changed records. Each repository would need to maintain data base pointers that identify records by date and time entered or changed so that other search repositories only need to retrieve that information and not all records. Again, similar methods are used by search bots to avoid retrieving unnecessary data.

Search for Patient Records in the Repository HCP<—>REP

Each repository could have a different interface or browser based method of allowing a HCP to query the data base of records in the repository. The basic process would be: (a) Obtain patient ID—Social security number or Alien ID; (b) Scan database for records for that patient ID; (c) Return list in a date order; and (d) For each record, indicate whether HCP can provide online access to further information.

Obtain detailed information about particular records HCP<—>REP<—>HCP

Medical records management systems have a local display method, often highly customized to the system itself and requiring extensive training to use effectively to obtain and display patient information. Vendors of these systems would be encouraged to provide a standard means of displaying information to other HCPs using browser based tools and readily available display methods. New and improved records management systems will include as a standard process external access that does not require specialized training or skills in each system, to make information available to other HCPs.

The method of accessing and displaying information would be contained in the repository database of HCPs. If a requesting HCP wants to see details from a treatment record, the repository would act as a translator to make the information available in readable and accessible form. The exact format of record display and the methods available and employed by HCP record systems are expected to change and improve continually, but those changes would not affect the method employed herein because the method contemplates many different systems, having many different display methods.

Once a search has been performed by the requesting HCP and a list of available records displayed (steps 1-4 in the process above), a further process would be employed, as follows:

For each record, allow HCP to access or request information: (a) Directly into medical records system, if available, from the previous HCP; (b) Browser based display of information in standard format from previous HCP; (c) Request form to be forwarded to HCP requesting Fax or printed copies of medical records; and (d) Telephone and fax numbers of previous HCP if no other means of record retrieval available.

Figure 2:
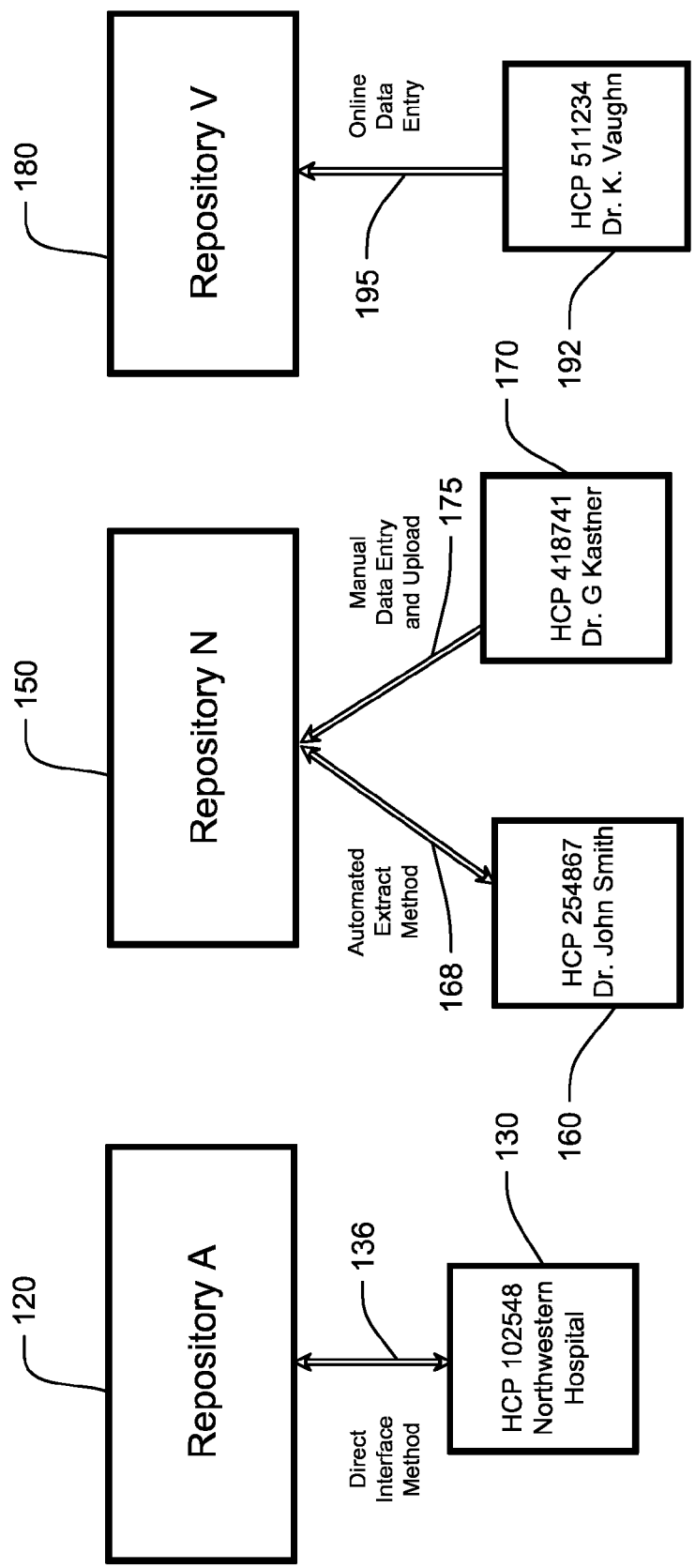
FIG. 2 is a general schematic overview of healthcare providers being capable of updating patient information medical links.

Referring now to FIG. 2, there is illustrated the various ways in which HCP update patient information to the Repositories for the creation of record pointers by the Repositories. Each of the Healthcare Providers (HCPs) from FIG. 1, is a subscriber or customer of Repositories A (120), N (150) or V (180), of many possible Repository Services Providers. Each HCP in the examples of this embodiment of the invention uses a different method to inform the Repository of patient records available in some form from the HCP. Northwestern Hospital (130) links (136) their recent electronic records management system directly to the repository, and allows for direct access to record information or images through the repository by other HCPs that may be treating a patient. The record pointers for every patient record can be updated hourly, and direct access to their computerized record system can be gained through repository A. Northwestern (130) also has in this example stored older records with the repository using a service provided by the repository. Dr. Smith (160) has a directly accessible system and updates the repository with patient record pointers daily (168). Dr. Smith can provide a browser based display of all patient records. Patient record pointers can be sent daily to the Repository N and his HCP information includes an indicator showing that other HCPs can view patient records via a browser. Dr. Kastner's (170) office uses an offline process to manually record information to upload to the repository (175). A spreadsheet may be used to record patient record pointers, which can be uploaded daily to the repository. His HCP information indicates that patient information can be faxed or mailed. Dr. Vaughn (192) indicates (195) the availability of records that could be mailed or faxed. Dr. Vaughn has indicated to Repository V that he has a number of patient records but does not provide detailed pointer information, only the latest date of record information by patient. As one possible convention, an HCP can indicate that many patient records are available by indicating a patient ID and the last service date, leaving the diagnostic or billing code blank.

Figure 3:
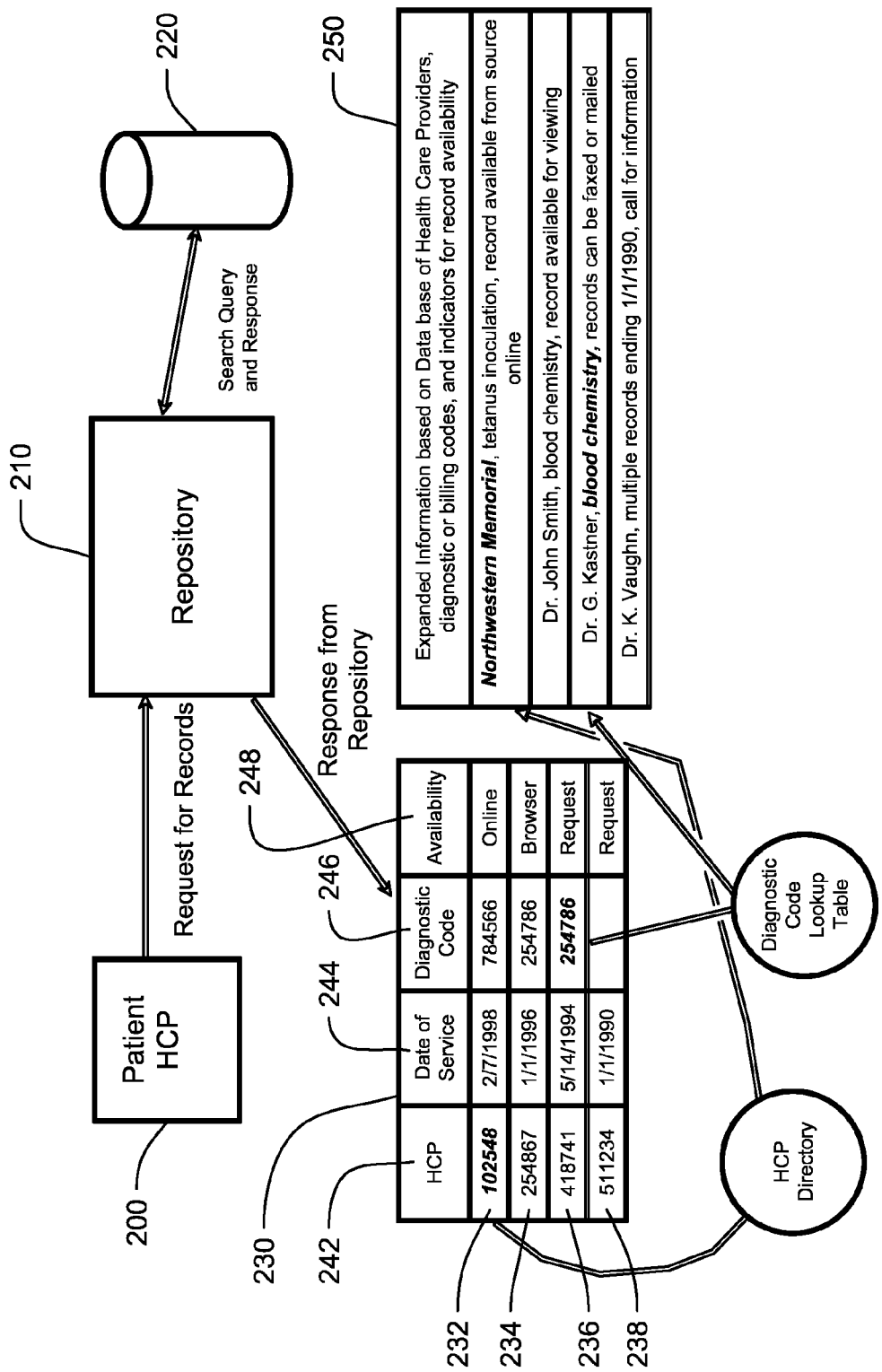
FIG. 3 is a general schematic overview of an example of a request for patient record information made by an healthcare provider.

Referring now to FIG. 3, there is shown an example of a request for patient record information by a Healthcare Provider 200 to a repository 210, and an example response. Upon receiving a request, the Repository conducts a search query 220 through its own records and through other repositories, if necessary. A response 230 to the search query is generated by the Repository and is either sent to the HCP or accessible/viewable by the HCP through a dedicated network. The response would include pointer records 232, 234, 236, 238. Each pointer record represents a medical record stored either on a repository 210 or at a HCP. Furthermore, each pointer record would typically include an HCP identification number 242, date of service 244, diagnostic or billing code 246, and the availability status 248. The availability status provides the searcher with information on how to retrieve the medical record. The response 230 may also provide for the ability for expanded information 250, based on the data base of HCP diagnostic or billing codes and indicators for record availability.

Advantageously, the record pointers contained in each health care record within a repository provide for a multitude of access methods to a multitude of record locations. For example, the access method definition in each pointer may represent any of the following: (1) technical parameters sufficient to enable direct access to the electronic record management system of the health care provider, and sufficient to enable the repository user to review all necessary and appropriate records that apply to the patient, the date of service and the diagnosis and/or billing code; (2) a URL that when issued by the repository can return an electronic image of one or more health care records as one or more web pages, including images such as x-rays or CAT scan captures; (3) a request form to be sent electronically to the health care provider identifying the patient, date of service and diagnostic codes/billing codes sufficient to allow the health care provider to identify, obtain and return the records and/or images to answer the request; and (4) a page of information that returns static information for the health care provider, such as the telephone number if a call is the only method of requesting copies of records, or a fax number if a faxed request can be initiated, to be used to request additional information or copies in multiple forms from the provider.

It is to be appreciated that any health care provider may have records in multiple forms: (i) older records on paper, (ii) newer records stored in an electronic records management system, or (iii) records archived in electronic form in a multitude of possible archives, said records capable of being accessed directly or with a URL and appropriate request parameters. Newer records are preferably capable of direct access by the repository user, particularly if record management software and system providers have adopted industry standards for external record access.

Also, in some embodiments, certain records may require additional validation or authorization if they are deemed sensitive and confidential by the patient or the health care provider. For example, some psychiatric records may not be available to treating physicians even though the psychiatric diagnosis and medications may conflict with treatment options considered by the treating physician. In such a case, the existence of these records would be shown in the repository, for example, with a generic diagnosis code but indicating prescriptions issued, sufficient to indicate to the treating physician that follow-up may be needed before prescribing medications or treatment that may be contra-indicated.

In each case, it is important that every treatment, diagnosis, billing code and medical information source be present in the repository along with the access method: direct, URL image, electronic request form, fax or telephone.

Based on the above disclosure and drawings, there is provided herein one or more embodiments for creating and accessing patient medical information in a network. In one embodiment there is provided a repository database storing medical records of a plurality of patients. Each medical record would be associated with a healthcare provider and further includes a healthcare provider identification code, a date of service, a diagnostic or billing code, and an availability code listing the access of the medical record with the respect to the healthcare provider. A search processor is included for initiating, in response to a first command, a search of the repository database to locate at least one medical record associated with a particular patient. In addition, an interface processor is included for generating in response to a second command, a request to access the stored medical record of the particular patient. The response to the second command would include at least one of the following: a link to the actual medical record being stored on the repository database, or direct contact information associated with the healthcare provider. To separate the medical records efficiently, each patient, of the plurality of patients, is associated with a patient identifier. In this embodiment the direct contact information associated with the healthcare provider would either be a telephone number, email, or facsimile number.

In other embodiments, there would be provided a plurality of repository databases, each storing medical records of a plurality of patients, and wherein the search processor for initiating, in response to the first command, searches the plurality of repository databases, to locate all medical records associated with the particular patient.

In another embodiment there would be provided a system for accessing patient medical information in a network that included a plurality of repository databases storing medical links,. Each medical link would be associated to a medical record. The medical link includes a healthcare provider identification code, a date of service, a diagnostic or billing code, and an availability code listing the access of the medical record with the respect to the healthcare provider. An interface processor would be provided for generating a medical link in response to a generation command initiated by a healthcare provider having access to one or more of the repository databases, and wherein the generation of the medical link creates an availability code for the medical record, from one of the following: (a) a hyper-link to the medical record being stored on one of the repository databases, (b) a hyper-link to the medical record being stored on a healthcare provider database, or (c) non-networked direct contact information to the healthcare provider. In addition thereto, when the availability code indicating the medical record is non-networked direct contact information to the healthcare provider, the availability code further includes information associated with the healthcare provider such as but not limited to a telephone number, email, or facsimile number.

In view of the above, it will be seen that several advantages of the present invention have been achieved and other advantageous results have been obtained. From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred.

Source Code

The below represents source code that performs various functions including: (a) accepting updates from automated HCPs in the form of an XML file, a standard exchange method (others of course possible); (b) accepting updates through a web interface where an HCP would enter the information directly (non-automated HCPs); (c) providing updates to other Repositories using the XML file format, other methods of course possible; and (d) and allowing an HCP to query the repository file and see all records for a specific patient.

This routine creates sample versions of the three main data bases used in the Repository NManager process: RepDB has HCP records by patient, date of service and diagnostic code HCPDB is used to expand HCP codes to HCP names DiagnosticDB is used to expand diagnostic codes:

```
SetupandTestDB.java
package RepDemo;
import java.sql.Connection;
import java.sql.DriverManager;
import java.sql.ResultSet;
import java.sql.SQLException;
import java.sql.Statement;
import java.util.ArrayList;
import java.util.Properties;
import java.util.Scanner;
public class SetupandTestDB
/**
 * This routine creates sample versions of the three main
     data bases used
 * in the Repository NManager process:
 * RepDB has HCP records by patient, date of service and
     diagnostic code
 * HCPDB is used to expand HCP codes to HCP names
 * DiagnosticDB is used to expand diagnostic codes
 *
 */
public static void main(String[ ] args){
ArrayList<RecordPointer>recordpointers=new
    ArrayList<RecordPointer>( );
```

```
String recordpointersfilename="SamplePointers.XML";
Connection connection=null;
RecordPointer rp=null;
XMLDrivers xmldr=new XMLDrivers (recordpointers-
    filename, recordpointers);
SQLDrivers sqldr=new SQLDrivers(connection,rp);
BrowserDriver browserdr=new BrowserDriver (connec-
    tion);
SetupandTestDB.java
Properties props=new Properties( ); // connection proper-
    ties
// providing a user name and password is optional in the
    embedded
// and derbyclient frameworks
props.put("user", " ");
props.put("password", " ");
try {
connection=DriverManager.getConnection
    ("jdbc:derby:RepDB;", props);
if (!recordpointersTableExists(connection)){
if (!createRepDB(connection)) System.out.println("Cre-
    ate RepDB failed");
if (!createHCPDB(connection)) System.out.println("Cre-
    ate HCPDB failed");
if (!createDiagCodeDB(connection)) System.out.println
    ("Create Diagnostoc Code failed");
}
/*
*
*Read from the Sample XML file and insert into database
*
*/
recordpointers=xmldr.readXML    (recordpointersfile-
    name);
for (RecordPointer rpt: recordpointers){
if (!sqldr.insertintoDB(connection,rp1)) System.out.prin-
    tln("Insert failed");
}
/*
* Routine to create an XML exchange file to send to other
    reps
SetupandTestDB.java
* would normally use date of last exchange and update date
    of records
*/
recordpointersfilename="ExampleRepExchange.XML";
if (xmldr.writeXML
(recordpointers,recordpointersfilename))
System.out.println("XML File
"+recordpointersfilename+" successfully written");
/*
* Method to get records from a browser based data entry
    method
* This method would be used by manual or semiautomated
    HCPs
*
* HCPs with electronic systems would use XML file
    updates
* or other standard update process
*
... and the method to select records from the database and
* display them in date order, with
expanded explanations for
HCP and diagnostic code
*/
browserdr.getfrombrowser(connection);
String yn;
Scanner in=new Scanner(System.in);
System.out.println("Enter y to quit");
yn=in.nextLine( );
System.out.println("Leaving");
printRecordPointers(recordpointers);
}
SetupandTestDB.java
catch (SQLException sqle)
}
printSQLException(sqle);
}
if   (!dropDBTables(connection))   System.out.println
("table drop failed");
if (!disconnect( ) System.out.println("Disconnect failed");
}
private static boolean disconnect( )
{
try
{
// On a successful shutdown, this throws an exception
String shutdownURL="jdbc:derby:;shutdown=true";
DriverManager.getConnection(shutdownURL);
}
catch (SQLException e)
{
if (e.getMessage( )equals("Derby system shutdown."))
return true;
}
return false;
}
private static boolean createRepDB(Connection connec-
    tion)
{
String createDBString="CREATE TABLE RepDB ("
SetupandTestDB.java
+"HCPID VARCHAR(10),"
+"PatientID VARCHAR(11),"
+"DateofService VARCHAR(10),"
+"DiagnosticCode VARCHAR(10),"
+"Comment VARCHAR(40))";
try
{
Statement statement=connection.createStatement ( );
statement.execute(createDBString);
statement.close( );
System.out.println("RecordPointers    table    was
    created.\n");
return true;
}
catch (SQLException e)
{
e.printStackTrace( );
return false;
}
}
private static boolean createDiagCodeDB(Connection
    connection)
{
/*
* Sample diagnostic codes
* 813.46 Torus fracture of ulna (alone)
* 813.47 Torus fracture of radius and ulna
* V72.6 Laboratory examination
* V80.0 Special screening for neurological conditions
*/
String createDBString=
SetupandTestDB.java
```

```
"CREATE TABLE DiagCodeDB ("
+"DiagnosticCode VARCHAR(10),"
+"DiagnosticLong VARCHAR(50))";
try
{
Statement statement=connection.createStatement ( );
statement.execute(createDBString);
String insertString="INSERT INTO DiagCodeDB (Diag-
    nosticCode,DiagnosticLong)"+"VALUES  ('813.46',
    'Torus fracture of ulna (alone)')";
statement.execute(insertString);
insertString="INSERT INTO DiagCodeDB (Diagnostic-
    Code,DiagnosticLong)"+"VALUES  ('813.47','Torus
    fracture of radius and ulna')";
statement.execute(insertString);
statement.close( );
System.out.println("Diagnostic  Codes  table  was
    created.\n");
return true;
}
catch (SQLException e)
{
e.printStackTrace( );
return false;
}
}
private static boolean createHCPDB(Connection connec-
    tion)
{
String createDBString=SetupandTestDB.java "CREATE
    TABLE HCPDB ("+"HCPID VARCHAR(10),"+"HC-
    PLong VARCHAR(30))";
try
{
Statement statement=connection.createStatement ( );
statement.execute(createDBString);
String insertString="INSERT INTO HCPDB (HCPID,
    HCPLong)"+"VALUES  ('HCP123','Northwestern
    Memorial Hospital')";
statement.execute(insertString);
insertString="INSERT INTO HCPDB (HCPID,HC-
    PLong)"+"VALUES ('HCP456','Church Home and
    Hospital')"; statement.execute(insertString);
statement.close( );
System.out.println("HCP table was created.\n");
return true;
}
catch (SQLException e)
{
e.printStackTrace( );
return false;
}
}
public static boolean dropDBTables(Connection connec-
    tion)
}
String dropRepDBString="DROP TABLE RepDB";
String dropHCPDBString="DROP TABLE HCPDB";
String dropDiagCodeDBString="DROP TABLE Diag-
    CodeDB";
SetupandTestDB.java
try
{
Statement statement=connection.createStatement( );
statement.execute(dropRepDBString);
statement.execute(dropHCPDBString);
statement.execute(dropDiagCodeDBString);

System.out.println("RepDB tables were dropped.\n");
return true;
}
catch (SQLException e)
{
e.printStackTrace( );
return false;
}
}
public static boolean recordpointersTableExists (Connec-
    tion connection)
{
String  selectRecordPointersString="SELECT  HCPID
    FROM RepDB";
try
{
Statement statement=connection.createStatement ( );
ResultSet rs=statement.executeQuery (selectRecordPoint-
    ersString);
rs.next( );
statement.close( );
return true;
}
Page 8
SetupandTestDB.java
catch (SQLException e)
{
return false;
}
}
public static void printSQLException(SQLException e)
{
// Unwraps the entire exception chain to unveil the real
    cause of the
// Exception.
while (e !=null)
{
System.err.println("\n - - - SQLException - - -");
System.err.println("SQL State:"+e.getSQLState( );
System.err.println("Error Code:"+e.getErrorCode( );
System.err.println("Message:"+e.getMessage( );
// for stack traces, refer to derby.log or uncomment this:
//e. printStackTrace(System.err);
e=e.getNextException( );
}
}
private static void printRecordPointers
(ArrayList<RecordPointer>recordpointers)
{
for (RecordPointer p: recordpointers)
{
printRecordPointer(p);
}
System.out.println( )
}
SetupandTestDB.java
private static void printRecordPointer(RecordPointer p)
{
System.out.println(p.getHCP( )+p.getPatientID( )+p.get-
    DateofService( )+p.getDiagnosticCode( )+p.getCom-
    ment( );
}
}
```

The following code outlines the method of accepting records entered online and adds the record pointer file. It further selects records from the Repository database based on patient ID and displays the results in a list:

```
BrowserDriver.java
package RepDemo;
import java.awt.*;
/**
 * getfrombrowser method accepts record entered online
 * and adds it to the record pointer file.
 *
 * showinbrowser selects records from the Repository database
 * based on patient ID and displays the results in a list
 *
 * Gordon Kerr
 * 11/29/2009 through 12/13/2009
 *
 */
public class BrowserDriver {
RecordPointer rp=new RecordPointer( );
private Connection connection;
String patientID=null;
ArrayList<String>patientrecords=new ArrayList<String>( );
public   BrowserDriver(Connection   connection) {this.connection=connection;
}
SQLDrivers sqldr=new SQLDrivers(connection, rp);
public void getfrombrowser(Connection connection) {
this.connection=connection;
JFrame frame=new RecordPointerFrame( );
BrowserDriver.java
frame.setVisible(true);
return;
}
public class RecordPointerFrame extends JFrame
{
private static final long serialVersionUID=1L;
public RecordPointerFrame( )
{
setTitle("Enter HC Records");
centerWindow(this);
setSize(800,450);
setResizable(false);
setDefaultCloseOperation(JFrame.EXIT_ON_CLOSE);
JPanel panel=new RecordPointerPanel( );
this.add(panel);
}
private void centerWindow(Window w)
{
Toolkit tk=Toolkit.getDefaultToolkit( );
Dimension d=tk.getScreenSize( );
setLocation((d.width-w.getWidth( )/2, (d.heightw. getHeight( )/2);
}
}
class RecordPointerPanel extends JPanel implements Action Listener
{
/**
 *
 */
private static final long serialVersionUID=1L;
private JPanel displayPanel=new JPanel( );
BrowserDriver.java
private JTextField HCPIDTextField,
patientIDTextField,
dateofserviceTextField,
diagnosticcodeTextField,
commentTextField,
HCPIDerrorTextField,
patientIDerrorTextField,
dateofserviceerrorTextField,
diagnosticcodeerrorTextField,
legendTextField;
private JLabel HCPIDLabel,
patientIDLabel,
dateofserviceLabel,
diagnosticcodeLabel,
commentLabel;
private JList record List;
private JButton addrecordButton,
getpatientrecordsButton,
exitButton;
DefaultListModel recordListModel=new DefaultListModel( );
private boolean addingPatientRecordsMode;
public RecordPointerPanel( )
{
// display panel
displayPanel.setLayout(new  FlowLayout  (FlowLayout. RIGHT));
// HCPID label
HCPIDLabel=new JLabel("HCPID");
displayPanel.add(HCPIDLabel);
// HCPID text field
HCPIDTextField=new JTextField(10);
BrowserDriver.java
displayPanel.add(HCPIDTextField);
HCPIDerrorTextField=new JTextField(40);
HCPIDerrorTextField.setEditable(false);
HCPIDerrorTextField.setFocusable(false);
displayPanel.add(HCPIDerrorTextField);
// Patient ID label patientIDLabel=new JLabel("Patient ID");
displayPanel.add(patientIDLabel);
// Patient ID text field
patientIDTextField=new JTextField(11);
displayPanel.add(patientIDTextField);
patientIDerrorTextField=new JTextField(39);
patientIDerrorTextField.setEditable(false);
patientIDerrorTextField.setFocusable(false);
displayPanel.add(patientIDerrorTextField);
// Date of Service label
dateofserviceLabel=new JLabel("Date of Service");
displayPanel.add(dateofserviceLabel);
// Date of Service text field
dateofserviceTextField=new JTextField(10);
displayPanel.add(dateofserviceTextField);
dateofserviceerrorTextField=new JTextField (40);
dateofserviceerrorTextField.setEditable(false);
dateofserviceerrorTextField.setFocusable(false);
displayPanel.add(dateofserviceerrorTextField);
// Diagnostic Code label
diagnosticcodeLabel=new JLabel("Diagnostic Code");
displayPanel.add(diagnosticcodeLabel);
BrowserDriver.java
// Diagnostic Code text field
diagnosticcodeTextField=new JTextField(10);
displayPanel.add(diagnosticcodeTextField);
diagnosticcodeerrorTextField=new JTextField (40);
diagnosticcodeerrorTextField.setEditable(false);
diagnosticcodeerrorTextField.setFocusable (false);
displayPanel.add(diagnosticcodeerrorTextField);
// Comments label
commentLabel=new JLabel("Comments");
displayPanel.add(commentLabel);
```

```
// Comments text field
commentTextField=new JTextField(50);
displayPanel.add(commentTextField);
// Legend text field describing record
   information in scroll pane
// either records added or records for patient ID
legendTextField=new JTextField(60);
legendTextField.setEditable(false);
legendTextField.setFocusable(false);
displayPanel.add(legendTextField);
// Show patient records in scroll pane
recordList=new JList(recordListModel);
recordList.setFixedCellWidth(700);
recordListsetSelectedIndex(0);
recordList.setVisibleRowCount(10);
JScrollPane recordscroll=new JScrollPane (recordList);
displayPanel.add(recordscroll);
BrowserDriver.java
// button panel
JPanel buttonPanel=new JPanel( );
buttonPanel.setLayout(new FlowLayout (FlowLayout.
   RIGHT));
// Add Record button
addrecordButton=new JButton("Add Record");
addrecordButton.addActionListener(this);
buttonPanel.add(addrecordButton);
// Add Get Patient ID button
getpatientrecordsButton=new JButton("Get Records for
   Patient");
getpatientrecordsButton.addActionListener(this);
buttonPanel.add(getpatientrecordsButton);
// exit button
exitButton=new JButton("Exit");
exitButton.addActionListener(this);
buttonPanel.add(exitButton);
// add panels to main panel
this.setLayout(new BorderLayout( ));
this.add(displayPanel, BorderLayout.CENTER);
this.add(buttonPanel, BorderLayout.SOUTH);
//this.add(new JScrollPane(recordList), BorderLayout.
   CENTER);
}
public void actionPerformed(ActionEvent e)
{
Object source=e.getSource( );
if (source==exitButton) System.exit(0);
BrowserDriver.java
else if (source==addrecordButton){
legendTextField.setText("Records Added So Far");
if (!addingPatientRecordsMode)
while (recordListModel.getSize( )!=0)
recordListModel.remove(0);
addingPatientRecordsMode=true;
String hcp=HCPIDTextField.getText( );
rp.setHCP(hcp);
String patientID=patientIDTextField.getText( );
rp.setPatientID(patientID);
String dateofservice=dateofserviceTextField.getText( );
rp.setDateofService(dateofservice);
String diagnosticcode=diagnosticcodeTextField.getText(
   );
rp.setDiagnosticCode(diagnosticcode);
diagnosticcodeTextField.setText(" ");
String comment=commentTextField.getText( );
rp.setComment(comment);
commentTextField.setText(" ");
sqldr.insertintoDB(connection,rp);
recordListModel.addElement(hcp+patientID +dateofser-
   vice+diagnosticcode+comment);
}
else if (source==getpatientrecordsButton){
// clear list and reset legend to note panel
   contains patient records retrieved
if (addingPatientRecordsMode)
while (recordListModel.getSize( )!=0)
recordListModel.remove(0);
addingPatientRecordsMode=false;
patientID=patientIDTextField.getText( );
legendTextField.setText("Records retrieved for Patiend
   ID"+patientID);
BrowserDriver.java
patientrecords=sqldr.selectfrom DB (connection,patien-
   tID);
// Scroll List
if (patientrecords.size( )==0)
System.out.println("Select returned no records for patien-
   tID"+patientID);
for (String s: patientrecords)
recordListModel.addElement(s);
recordList.setSelectedIndex(0);
}
}
}
}
   The following code implements SQL routines to add
records to the database and select records from the database
based on a patient ID:
   SQLDrivers.java
   package RepDemo;
   import java.sql.*;
   /*
   * Implements SQL routines to add records to the database
   * and select records from based on patient ID
   *
   * insertintoDB( )adds a record of class RecordPointer
   * selectfromDB( )issues a select statement based on patient
      ID and uses
   * inner joins to return expanded values for hcpID and
      diagnostic code
   * from tables containing those reference records
   *
   * Gordon Kerr
   * 12/02/2009
   *
   */
   public class SQLDrivers{
   Connection connection;
   ArrayList<RecordPointer>recordpointers;
   RecordPointer rp;
   String patientID;
   public SQLDrivers(Connection connection, Record-
      Pointer rp){
   this.connection=connection;
   this.rp=rp;
   }
   public SQLDrivers(Connection connection,String patien-
      tID){
   this.connection=connection;
   this.patientID=patientID;
   }
   SQLDrivers.java
   public boolean insertintoDB(Connection connection,
      Record Pointer rp)
   {
```

```
this.connection=connection;
this.rp=rp;
String  insertRecordPointerString="INSERT  INTO
    RepDB"+"VALUES ("'"+rp.getHCP( )+"'", "'"+rp.getPa-
    tientID ( )+"'","'"+rp.getDateofService( )+"'", "'"+rp.getDi-
    agnosticCode( )+"'", "'"+rp.getComment( )"'")";
try
{
Statement statement=connection.createStatement ( );
statement.execute(insertRecordPointerString);
statement.close( );
return true;
}
catch (SQLException e)
{
e.printStackTrace( );
return false;
}
}
public ArrayList<String>selectfromDB(Connection con-
    nection,String patientID)
{
this.connection=connection;
this.patientID=patientID;
String selectRecordPointerString="SELECT HCPLong,
    PatientID,DateofService,"+SQLDrivers.java
"DiagnosticLong,Comment FROM RepDB "+" INNER
    JOIN HCPDB ON RepDB.HCPID=HCPDB.HCPID"+
    "INNER JOIN DiagCodeDB on RepDB.Diagnostic-
    Code"+
"DiagCodeDB.DiagnosticCode"+"WHERE    Patien-
    tID="'"+patientID+"'"  ORDER  BY  DateOfService
    DESC";
try
{
Statement statement=connection.createStatement ( );
ResultSet rs=statement.executeQuery (selectRecordPoint-
    erString);
//convert result set to array list form
ArrayList<String>patientrecords=new
    ArrayList<String>( );
while (rs.next( )){
patientrecords.add(rs.getString(1)+",
"+rs.getString(2)+", "+rs.getString(3)+", "+rs.getString
    (4)+", "+rs.getString(5));
}
rs.close( );
statement.close( );
System.out.println(patientrecords);
return patientrecords;
}
catch (SQLException e)
{
e.printStackTrace( );
return null;
}
}
}
The following code is used to import record pointer infor-
mation from the healthcare providers and export the informa-
tion to the repositories:
    XMLDrivers.java
    package RepDemo;
    import java.util.ArrayList;
/**
* XMLDrivers manages reading and writing XML files
*
* Used to import Record Pointer information from HCR's
    and export to Reps
*
* Gordon Kerr
* 11/28/2009
* Moved to Eclipse in new version 12/3/2009
*/
public class XMLDrivers{
String filename;
ArrayList<RecordPointer>recordpointers;
File recordpointersFile=null;
public XMLDrivers(String recordpointersfilename,
    ArrayList<RecordPointer>recordpointers){
this.filename=recordpointersfilename;
this.recordpointers=recordpointers;
recordpointersFile=new File(filename);
}
private void checkFile( )throws IOException
{
// if the file doesn't exist, create it
if (!recordpointersFile.exists( ))
recordpointersFile.createNewFile( );
}
public boolean writeXML(ArrayList<RecordPointer>
recordpointers,
XMLDrivers.java
public boolean writeXML(ArrayList<RecordPointer>
recordpointers,
String recordpointersfilename){
this.filename=recordpointersfilename;
this.recordpointers=recordpointers;
recordpointersFile=new File(filename);
// create the XMLOutputFactory object
XMLOutputFactory
    outputFactory=XMLOutputFactory.newInstance( );
try
{
// make sure the file exists
this.checkFile( );
System.out.println("Writing XML file"+filename);
// create XMLStreamWriter object
FileWriter fileWriter=new FileWriter(filename);
XMLStreamWriter
    writer=outputFactory.createXMLStreamWriter   (file-
    Writer);
//write the record pointers to the file
writer.writeStartDocument("1.0");
writer.writeStartElement("RecordPointers");
for (RecordPointer rp: recordpointers)
{
writer.writeStartElement("RecordPointer");
writer.writeAttribute("HCP", rp.getHCP( ));
writer.writeStartElement("PatientID");
writer.writeCharacters(rp.getPatientID( ));
XMLDrivers.java
writerwriteEndElement( );
writer.writeStartElement("DateofService");
writer.writeCharacters(rp.getDateofService ( ));
writerwriteEndElement( );
writerwriteStartElement("DiagnosticCode");
writer.writeCharacters(rp.getDiagnosticCode ( ));
writerwriteEndElement( );
writerwriteStartElement("Comment");
writer.writeCharacters(rp.getComment( );
writerwriteEndElement( );
writerwriteEndElement( );
}
```

```
writerwriteEndElement( );
writerflush( );
writer.close( );
}
catch (IOException e)
{
e.printStackTrace( );
return false;
}
catch (XMLStreamException e)
{
e.printStackTrace( );
return false;
}
return true;
}
XMLDrivers.java
public ArrayList<RecordPointer>readXML(String filename)
{
// code to implement method for readXML
//this.filename=filename;
ArrayList<RecordPointer>recordpointers=new ArrayList<RecordPointer>( );
RecordPointer rp=null;
// create the XMLInputFactory object
XMLInputFactory
    inputFactory=XMLInputFactory.newInstance( );
try
{
// create a XMLStreamReader object
FileReader fileReader=new FileReader(filename);
XMLStreamReader
    reader=inputFactory.createXMLStream Reader
    (fileReader);
// read the recordpointers from the file
while (reader.hasNext( ))
{
int eventType=reader.getEventType( );
switch (eventType)
{
case XMLStreamConstants.START_ELEMENT:
String elementName=readergetLocalName( );
if (elementName.equals
("RecordPointer"))
{
rp=new RecordPointer( );
XMLDrivers.java
String hcp=reader.getAttributeValue(0);
rp.setHCP(hcp);
}
if (elementName.equals("PatientID"))
{
String patientID=reader.getElementText( );
rp.setPatientID(patientID);
}
if (elementName.equals
("DateofService"))
{
String dateofservice=reader.getElementText( )
rp.setDateofService
(dateofservice);
}
if (elementName.equals
("DiagnosticCode"))
{
String diagnosticcode=reader.getElementText( );
rp.setDiagnosticCode
(diagnosticcode);
}
if (elementName.equals("Comment"))
{
String comment=reader.getElementText( );
rp.setComment(comment);
}
break;
case XMLStreamConstants.END_ELEMENT:
elementName=reader.getLocalName( );
XMLDrivers.java
if (elementName.equals
("RecordPointer"))
{
recordpointers.add(rp);
}
break;
default:
elementName=reader.getLocalName( );
break;
}
readernext( );
}
}
catch (IOException e)
{
e.printStackTrace( );
return null;
}
catch (XMLStreamException e)
{
e.printStackTrace( );
return null;
}
return recordpointers;
}
}
```

The invention claimed is:

1. A computer-based system for accessing patient medical information in a network comprising:
at least one repository computing device, said at least one repository computing device configured and arranged to receive and process a plurality of medical record pointers uploaded and generated by at least one healthcare provider computing device, said medical record pointers including summary information sufficient to locate detailed medical records about one or more patients, without including the entire content of said detailed medical records themselves;
at least one repository database residing on said at least one repository computing device, said at least one repository database storing a plurality of medical links, each medical link being associated to a medical record that is associated to a patient by a unique patient identifier, each medical link including at least one of: (i) a healthcare provider identification code, (ii) a date of service, and (iii) a diagnostic or billing code, each medical link further including an availability code, said availability code includes a listing of an ability to access the medical record with the respect to the healthcare provider; and
an interface processor, which includes a computer hardware component, for generating a medical link in response to a generation command initiated by a healthcare provider having access to said at least one repository database, and wherein the generation of the medical link creates an availability code for the medical record, from one of the following:
(a) a hyper-link to the medical record being stored on said at least one repository database,
(b) a hyper-link to the medical record being stored on a healthcare provider database, and/or
(c) direct contact information to the healthcare provider.

2. The computer-based system of claim 1, wherein, when the availability code indicates the medical record is direct contact information to the healthcare provider, the availability code further includes information associated with the healthcare provider, including one or more of the following: (i) a telephone number, (ii) email, or (iii) facsimile number.

3. The computer-based system of claim 2 further comprising:
a search processor, which includes a computer hardware component, for initiating, in response to a first command, a search of said at least one repository database to locate at least one medical record associated with a particular patient; and
wherein said interface processor further generates in response to a second command, a request to access said at least one medical record of the particular patient, which said response to said second command includes at least one of the following: a link to the actual medical record being stored on said at least one repository database or stored on said healthcare provider database, or direct contact information associated with the healthcare provider.

4. The computer-based system of claim 1, wherein said at least one repository computing device includes an updating processor for communicating and updating with other repository computing devices medical links generated thereon.

5. The computer-based system of claim 1, wherein a healthcare provider is capable of updating healthcare records in said at least one repository database.

6. The computer-based system of claim 3, wherein said at least one repository database comprises a plurality of repository databases, each of said plurality of repository databases storing and exchanging medical records of a plurality of patients with each other of said plurality of repository databases, and wherein said search processor for initiating, in response to said first command, searches a repository database, of said plurality of repository databases, to locate all medical records associated with the particular patient.

7. The computer-based system of claim 3, wherein each said medical link includes a respective diagnostic or billing code, and said diagnostic or billing code is linked to detailed information in the medical record, such that said interface processor upon the request to access said stored medical record of the particular patient, retrieves the detailed information for display.

8. A computer-based system for accessing patient medical information in a network comprising:
at least one repository computing device, said at least one repository computing device configured and arranged to receive and process a plurality of medical record pointers uploaded and generated by at least one healthcare provider computing device, said medical record pointers including summary information sufficient to locate detailed medical records about one or more patients, without including the entire content of said detailed medical records themselves;
at least one repository database residing on said at least one repository computing device, said at least one repository database storing a plurality of medical links, each medical link being associated to a medical record that is associated to a patient by a unique patient identifier, each medical link including at least one of: (i) a healthcare provider identification code, (ii) a date of service, and (iii) a diagnostic or billing code, each medical link further including an availability code, said availability code includes a listing of an ability to access the medical record with the respect to the healthcare provider; and
an interface processor, which includes a computer hardware component, for generating a medical link in response to a generation command initiated by a healthcare provider having access to said at least one repository database, and wherein the generation of the medical link creates an availability code for the medical record listing an ability to access the medical record with the respect to the healthcare provider.

9. The computer-based system of claim 8, wherein a healthcare provider is capable of updating healthcare records in said at least one repository database.

10. The computer-based system of claim 8 further comprising:
a search processor, which includes a computer hardware component, for initiating, in response to a first command, a search of said at least one repository database to locate at least one medical record associated with a particular patient; and
wherein said interface processor further generates in response to a second command, a request to access said at least one medical record of the particular patient, which said response to said second command includes at least one of the following: a link to the actual medical record being stored on said at least one repository database or stored on a healthcare provider database, or direct contact information associated with the healthcare provider.

11. The computer-based system of claim 10, wherein each said medical link includes a respective diagnostic or billing code, and said diagnostic or billing code is linked to detailed information in the medical record, such that said interface processor upon the request to access said stored medical record of the particular patient, retrieves the detailed information for display.

12. A computer-based system for accessing patient medical information in a network comprising:
a plurality of repository computing devices, each of said plurality of repository computing devices configured and arranged to receive and process a plurality of medical record pointers uploaded and generated by a plurality of healthcare provider computing devices, said medical record pointers including summary information sufficient to locate detailed medical records about one or more patients, without including the entire content of said detailed medical records themselves;
a plurality of repository databases, a first of said plurality of repository databases residing on a first of said plurality of repository computing devices and a second of said plurality of repository databases residing on a second of said plurality of repository computing devices, each of said plurality of repository databases storing medical links, each medical link being associated to a medical record that is associated to a patient by a unique patient identifier, each medical link including at least one of: (i) a healthcare provider identification code, (ii) a date of service, and (iii) a diagnostic or billing code, each medical link further including an availability code, said availability code includes a listing of an ability to access the medical record with respect to the healthcare provider; and an interface processor, which includes a computer hardware component, for generating a medical link in response to a generation command initiated by a healthcare provider having access to one of said plurality of repository databases, and wherein the generation of the medical link creates an availability code for the medical record listing an ability to access the medical record with respect to the healthcare provider.

13. The computer-based system of claim 12 further comprising:

a search processor, which includes a computer hardware component, for initiating, in response to a first command, a search of one of said plurality of repository databases to locate at least one medical record associated with a particular patient; and wherein said interface processor further generates in response to a second command, a request to access said at least one medical record of the particular patient, which said response to said second command includes at least one of the following: a link to the actual medical record being stored on said one of said plurality of repository databases or stored on a healthcare provider database, or direct contact information associated with the healthcare provider.

14. The computer-based system of claim 13, wherein each of said plurality of repository databases stores and exchanges medical records of a plurality of patients with each other of said plurality of repository databases, and wherein said search processor for initiating, in response to said first command, searches a repository database, of said plurality of repository databases, to locate all medical records associated with the particular patient.

15. The computer-based system of claim 13, wherein each said medical link includes a respective diagnostic or billing code, and said diagnostic or billing code is linked to detailed information in the medical record, such that said interface processor upon the request to access said stored medical record of the particular patient, retrieves the detailed information for display.

16. The computer-based system of claim 12, wherein said first repository computing device is configured and arranged to exchange said medical links with said second repository computing device.

17. The computer-based system of claim 12, wherein a healthcare provider is capable of updating healthcare records in one of said plurality of repository databases.

18. The computer-based system of claim 12, wherein the generation of the medical link creates an availability code for the medical record, from one of the following:
  (a) a hyper-link to the medical record being stored on one of said plurality of repository databases,
  (b) a hyper-link to the medical record being stored on a healthcare provider database, and/or
  (c) direct contact information to the healthcare provider.

19. The computer-based system of claim 18, wherein, when the availability code indicates the medical record is direct contact information to the healthcare provider, the availability code further includes information associated with the healthcare provider, including one or more of the following: (i) a telephone number, (ii) email, or (iii) facsimile number.

20. The computer-based system of claim 12, wherein at least one of said plurality of repository computing devices includes an updating processor for communicating and updating with other said repository computing devices medical links generated thereon.

* * * * *